(12) United States Patent
Moeller

(10) Patent No.: US 10,166,372 B2
(45) Date of Patent: Jan. 1, 2019

(54) ANGIOPLASTY BALLOON IMPROVED WITH GRAPHENE

(71) Applicant: Cook Medical Technologies LLC, Bloomington, IN (US)

(72) Inventor: Rasmus Buch Moeller, Ringsted (DK)

(73) Assignee: Cook Medical Technologies LLC, Bloomington, IN (US)

( * ) Notice: Subject to any disclaimer, the term of this patent is extended or adjusted under 35 U.S.C. 154(b) by 249 days.

(21) Appl. No.: 14/724,186

(22) Filed: May 28, 2015

(65) Prior Publication Data

US 2015/0352335 A1 Dec. 10, 2015

Related U.S. Application Data

(60) Provisional application No. 62/008,979, filed on Jun. 6, 2014.

(51) Int. Cl.
*A61M 29/00* (2006.01)
*A61M 25/10* (2013.01)
*A61L 29/10* (2006.01)

(52) U.S. Cl.
CPC ......... *A61M 25/104* (2013.01); *A61L 29/103* (2013.01); *A61M 25/1029* (2013.01); *A61M 2025/1075* (2013.01); *A61M 2025/1084* (2013.01)

(58) Field of Classification Search
CPC ............ A61M 25/104; A61M 25/1029; A61M 29/02; A61M 29/00; A61M 2025/1075; A61M 2025/1084; A61M 2025/0216; A61M 25/10; A61F 2/958
See application file for complete search history.

(56) References Cited

U.S. PATENT DOCUMENTS

| | | |
|---|---|---|
| 6,213,975 B1 | 4/2001 | Laksin |
| 6,331,265 B1 | 12/2001 | Dupire et al. |
| 7,037,319 B2 | 5/2006 | Weber |
| 7,172,796 B2 | 2/2007 | Kinoshita et al. |
| 7,517,353 B2 | 4/2009 | Weber |
| 7,758,572 B2 | 7/2010 | Weber et al. |
| 7,758,892 B1 | 7/2010 | Chen et al. |
| 7,942,847 B2 | 5/2011 | Stupecky et al. |
| 8,187,221 B2 | 5/2012 | Bates |
| 8,480,729 B2 | 7/2013 | Atanasoska et al. |
| 8,518,507 B2 | 8/2013 | Jimenez |
| 2005/0027248 A1 | 2/2005 | Suzuki et al. |
| 2007/0191766 A1 | 8/2007 | McMorrow |
| 2007/0244501 A1 | 10/2007 | Horn et al. |
| 2009/0068244 A1 | 3/2009 | Weber et al. |
| 2009/0299327 A1 | 12/2009 | Tilson et al. |

(Continued)

FOREIGN PATENT DOCUMENTS

WO WO 2013/083999 6/2013

*Primary Examiner* — Victor Nguyen
(74) *Attorney, Agent, or Firm* — Eric D. Babych; Brinks Gilson & Lione

(57) ABSTRACT

Inflatable medical balloons are disclosed herein. The inflatable medical balloons include balloon walls that are reinforced with graphene. The balloon walls can include any number of layers and one or more of the layers may include graphene. Catheters including the medical balloons are also disclosed in addition to methods for manufacturing the inflatable medical balloons.

18 Claims, 1 Drawing Sheet

(56) References Cited

U.S. PATENT DOCUMENTS

| | | | |
|---|---|---|---|
| 2010/0010470 A1* | 1/2010 | Bates | A61L 29/126 |
| | | | 604/509 |
| 2010/0158193 A1 | 6/2010 | Bates | |
| 2011/0046711 A1 | 2/2011 | Degen et al. | |
| 2012/0016297 A1 | 1/2012 | D'Aquanni et al. | |
| 2012/0142832 A1 | 6/2012 | Varma et al. | |
| 2013/0331927 A1* | 12/2013 | Zheng | A61F 2/82 |
| | | | 623/1.19 |

* cited by examiner

ANGIOPLASTY BALLOON IMPROVED WITH GRAPHENE

CROSS-REFERENCE TO RELATED APPLICATIONS

The present application claims the benefit of U.S. Provisional Patent Application No. 62/008,979, filed Jun. 6, 2014, the contents of which are incorporated into the present application in their entirety.

BACKGROUND

1. Field of the Invention

The present disclosure generally relates to medical devices. More particularly, the disclosure relates to reinforced medical balloons.

2. Description of the Related Art

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow).

Although balloon catheters are used in many other procedures as well, coronary angioplasty using a balloon catheter has drawn particular attention from the medical community because of the growing number of people suffering from heart problems associated with stenosis. Angioplasty procedures have become a popular alternative for treating coronary stenosis because such procedures are considerably less invasive than other alternatives. For example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery.

Typically, angioplasty procedures are performed using a balloon-tipped catheter that may or may not have a stent mounted on the balloon (also referred to as a stented catheter). The physician may perform the angioplasty procedure by inserting a guide wire into a patient's body (commonly through one of the arteries in the leg) and navigating the guide wire to a diseased area. A balloon catheter may then be inserted over the guide wire and guided to the diseased area, such as a narrowed part of a coronary artery. During this stage, the balloon is uninflated and collapsed onto the shaft of the catheter in order to present a low profile which may be passed through the arterial lumens. Once the balloon is positioned at the narrowed part of the artery, the balloon is expanded by pumping an inflation solution through the catheter to the balloon. As a result, the balloon presses against the inner wall of the artery to cause dilation.

Typical inflated pressures of the balloon may range between about 6 atm to about 20 atm (i.e., 90 psi-300 psi). If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the body. If a stent is mounted on the balloon of the catheter, the stent is left permanently implanted in its expanded state at the desired location in the artery to provide a support structure that prevents the artery from collapsing back to its pre-dilated condition. On the other hand, if the balloon catheter is not adapted for delivery of a stent, either a balloon-expandable stent or a self-expandable stent may be implanted in the dilated region in a follow-up procedure.

Examples of problems that may be encountered with conventional balloons relate to the balloon thickness and strength. A conventional balloon made from, for example, nylon 12 or polyethylene terephthalate (PET) may have a double wall thickness in the range of 0.04 mm to 0.1 mm. Due to the profile of such a balloon, there is limited access to certain areas of the body. Moreover, conventional materials may only allow for minimal inflation pressures and may burst if subjected to certain elevated pressures when such pressures are necessary to dilate, for example, a narrowed artery.

BRIEF SUMMARY

The present disclosure relates to inflatable medical balloons and methods of manufacturing the same. In one aspect, an inflatable medical balloon is provided, which comprises a balloon wall defining a balloon interior portion and a balloon exterior portion, wherein the balloon wall comprises an inner layer and an outer layer, and further wherein the outer layer comprises graphene.

In an additional aspect, an inflatable medical balloon is provided, which comprises a balloon wall defining a balloon interior portion and a balloon exterior portion, wherein the balloon wall consists essentially of graphene.

In a further aspect, an inflatable medical balloon is provided, which comprises a balloon wall defining a balloon interior portion and a balloon exterior portion, wherein the balloon wall comprises an inner layer and an outer layer, and further wherein the inner layer consists essentially of graphene.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

A detailed description of the invention is hereafter described with specific reference being made to the drawings in which.

DETAILED DESCRIPTION

Figure 1:
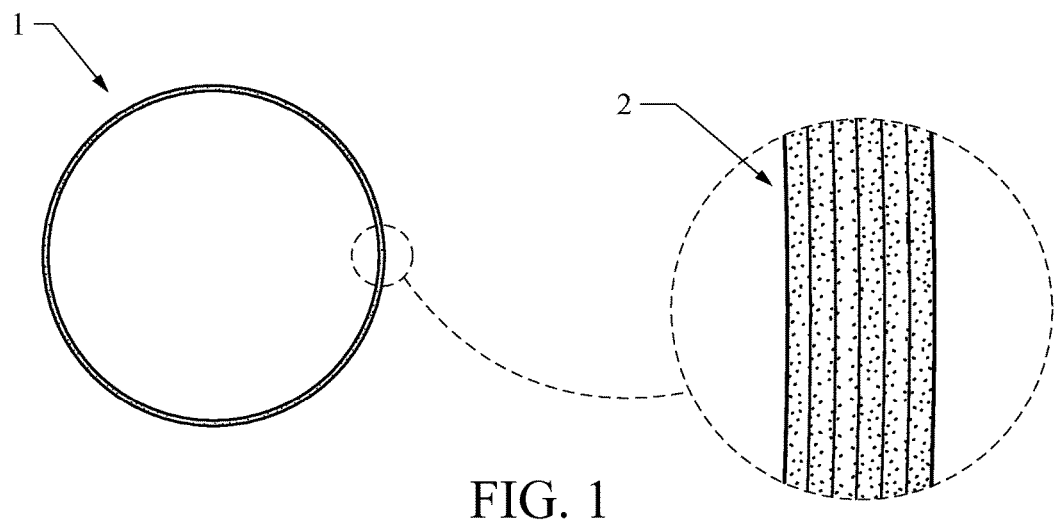
FIG. 1 shows a cross-section of an embodiment of the presently disclosed medical balloon having a balloon wall including graphene and an expanded view of the wall showing the balloon wall comprising multiple layers of graphene.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as conventional fabrication and assembly.

The present disclosure relates to medical balloons, methods for making such medical balloons, and potential applications for the medical balloons. The presently disclosed medical balloons may be used in a wide variety of medical applications such as, but not limited to, intraluminal procedures, angioplasty procedures such as angioplasty dilation of coronary or other arteries suffering from stenosis, temporary occlusion of large vessels, expansion of vascular prostheses, and stent delivery. The presently disclosed medical balloons are particularly suited for applications where a very low profile balloon is needed or where a balloon is needed that tolerates high pressures.

In some embodiments, the presently disclosed medical balloons include a balloon wall defining the medical balloon that may be manufactured from any materials known in the art for forming medical balloons. For example, the balloon/balloon wall may comprise silicone, PET, polyvinyl chloride, polypropylene, polyethylene, polyurethanes, polyamides, polyesters, latex, natural rubber, synthetic rubber, polyether block amides (such as Pebax™), and elastomers, mixtures, or copolymers thereof. In some embodiments, the balloon wall may comprise multiple layers, each layer comprising one or more of the aforementioned materials.

With respect to at least FIG. 1, in accordance with the present disclosure, the wall (1) of the medical balloon may further comprise graphene, consist essentially of graphene, or consist of graphene. Graphene is one of the crystalline forms of carbon where the carbon atoms are organized in a hexagonal pattern. It is often described as a 2 D material, meaning that it is a sheet having only one atom thickness of about 0.345 nm. Graphene is extremely strong, having a tensile strength of up to about 130 Gpa, and it is resiliant, which makes it ideal for inclusion in a medical balloon. Such medical balloon walls comprising graphene provide a very high strength to balloon wall thickness ratio which allows access to areas of the body previously inaccessable or areas that have been difficult to access using prior art balloons having higher profiles.

It is to be understood that in some instances, the use of the term "graphene" in the present application may be used interchangeably with "graphene sheet." It is also to be understood that the term "graphene" as used herein covers pure or native graphene in addition to modified graphene, such as graphene oxide or amide modified graphene.

Additionally, it is to be understood that in some instances, the component "graphene" may refer to a single graphene sheet or any number of layered graphene sheets, native or modified. For example, with respect to at least FIG. 1, a medical balloon wall (1) comprising graphene may include a single graphene sheet, or any number of layered graphene sheets (2), such as from about 1 to about 9,000 graphene sheets, from about 1 to about 6,000 graphene sheets, from about 1 to about 3,000 graphene sheets, from about 1 to about 140 graphene sheets, or from about 100 graphene sheets to about 3,000 graphene sheets.

In some embodiments, such as shown in FIG. 1, the medical balloon wall (1) is made solely from graphene, consists essentially of graphene, or consists of graphene. If the medical balloon wall consists essentially of graphene, it should be understood that the balloon wall includes graphene and any other components that do not materially affect the basic and novel characteristics of the balloon. In some embodiments, illustrative examples of components that would materially affect the basic and novel characteristics of the balloon include polymer binders and graphite. In certain embodiments, illustrative examples of components that would materially affect the basic and novel characteristics of the balloon include polymers. In some embodiments, illustrative examples of components that would materially affect the basic and novel characteristics of the balloon include carbon nanotubes, inorganic nanotubes, Kevlar™, Teflon™, Terlon™, Zylon™, polyether block amides, Vectran™, polymer binders, graphite, polymeric materials, thermoplastics, thermoset materials, silicone, polyethyleneterephthalate (PET), polyvinyl chloride, polypropylene, polyethylene, polyurethanes, polyamides, polyesters, latex, natural rubber, synthetic rubber, polyether block amides (such as Pebax™), and elastomers, mixtures, polymers, or copolymers thereof.

The balloon comprising, consisting essentially of, or consisting of graphene may have any desirable shape (e.g. cylindrical, circular, oval, etc.), such as any shape associated with a prior art medical balloon, but the balloon including graphene in its wall may have much thinner walls than prior art balloons. For example, since graphene is an extremely strong material, the thickness of the balloon wall comprising, consisting essentially of, or consisting of graphene may only need to be a few nanometers, such as from about 10 nm to about 5,000 nm, from about 50 nm to about 2,000 nm, from about from about 50 nm to about 1,000 nm, from about 100 nm to about 1,000 nm, from about 100 nm to about 500 nm, or from about 50 nm to about 500 nm. Theoretically, a balloon having a diameter of about 1.5 mm and a wall thickness of about 3.45 nm (which may equate to about 10 layers of graphene sheets) would have a burst pressure up to about 6 bars, assuming no defects and a tensile strength of 130 GPa.

Figure 2:
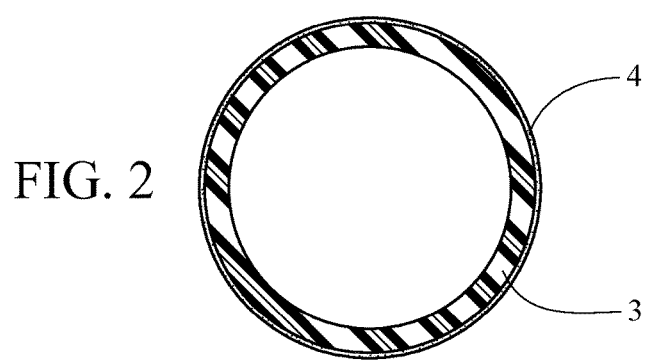
FIG. 2 shows a cross-section of an embodiment of the medical balloon having an outer layer including graphene.

In some embodiments, the medical balloon wall may comprise more than one layer. FIG. 2 shows such an embodiment wherein the wall includes an inner layer (3) comprising any known material for manufacturing medical balloons and an outer layer (4) comprising, consisting essentially of, or consisting of graphene. The balloon may comprise more than one outer layer and at least one of the outer layers, if not all of the outer layers, comprises, consists essentially of, or consists of graphene. In some embodiments, the inner layer may comprise, consists essentially of, or consist of graphene and any or all of the outer layers may also comprise, consists essentially of, or consist of graphene. For example, in one embodiment, the inner layer comprises, consists essentially of, or consists of graphene and the outer layer(s) comprises a polymer. Depending upon the desired properties of the balloon, if the wall of the balloon comprises, consists essentially of, or consists of graphene and a polymer, the thickness of the wall may be in the range from about 50 nm to about 40 μm.

Methods for manufacturing medical balloons comprising, consisting essentially of, or consisting of graphene are not particularly limited and can be chosen by one of ordinary skill in the art. For example, in one embodiment, using one or more sheets of graphene, the balloon may be synthesized on an exterior surface of a template (such as a mandrel). The template would have the desired shape of the balloon and the graphene sheet(s) would be disposed on the exterior surface of the template so that the graphene sheet(s) conformed to the shape of the template. After the synthesis is complete, the template may be removed, dissolved, melted, etc., and the balloon can then be, for example, mounted on a catheter.

Balloon catheters are well known in the art. A catheter may include a shaft having a proximal portion extending to a distal portion and a lumen formed therethrough. A medical balloon may be mounted at the distal end of the catheter. The medical balloon comprises a balloon wall defining a balloon interior portion and a balloon exterior portion. The balloon interior portion may be in fluid communication with the lumen of the shaft to allow for inflation/deflation of the balloon.

As an additional example, a number of smaller pieces of graphene may be used and these smaller pieces can be chemically linked together on a template to form the balloon/balloon wall. The graphene pieces may be chemically linked using any known methods in the art. For example, if the graphene was oxide modified graphene, one could cross-link the pieces together in water using polyallylamide and sonication. Again, after the synthesis is complete, the template may be removed, dissolved, melted, etc., and the balloon can then be, for example, mounted on a catheter for a medical application. The present application is not limited to any particular method for producing the medical balloon comprising, consisting essentially of, or consisting of graphene.

Since each perfect graphene sheet/layer is theoretically capable of providing 0.6 bars of burst strength for a 1.5 mm balloon, the present disclosure also contemplates adding one or more graphene layers to an existing balloon wall which does not otherwise comprise graphene. The number of graphene layers to be added is not particularly limited and appropriate numbers of layers have been discussed above. This would significantly improve the burst strength of the balloon compared to a balloon that does not comprise graphene in its wall. Manufacturing this type of balloon may be accomplished in a variety of different methods and the present disclosure is not limited to any particular method. As one example, one or more graphene sheets may simply be wrapped around a pre-existing balloon.

As an additional example, a balloon having one or more outer graphene layers may be formed in a single step process. For example, an outer layer comprising one or more graphene sheets may be positioned within a mold chamber prior to insertion of a polymer tube (parison). The parison may then be inserted and the mold and/or parison may be heated and inflation pressure may be fed into the lumen of the parison, thereby causing radial outward expansion of at least a mid-section of the parison in the mold.

The parison is heated to a temperature sufficient to cause its outer layers to soften. Thus, as the parison expands under the inflation pressure towards the walls of the mold, the graphene layer will become embedded, at least partially, onto an outer side of the expanded portion of the parison. Thus, by a single manufacturing process, the multiple-layer balloon can be formed within the mold.

Figure 3:
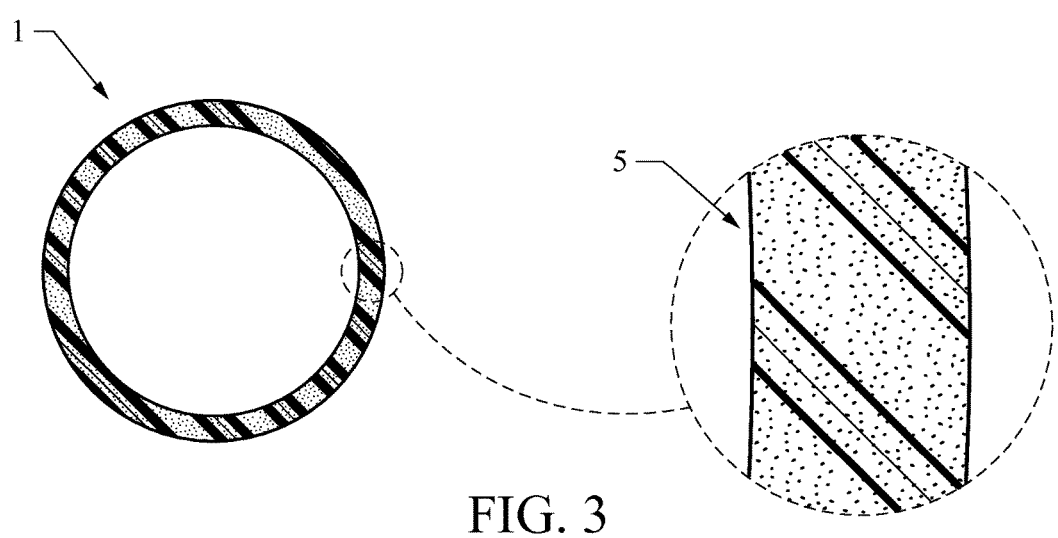
FIG. 3 shows a cross-section of an embodiment of the medical balloon having a balloon wall comprising a graphene-polymer matrix and an expanded view of the wall showing the polymer compounded with the graphene.

In additional embodiments, as can be seen in FIG. 3, one or more sheets of graphene may be compounded into a polymer matrix (5), thereby creating a composite. The polymer matrix is not limited and can comprise any polymer commonly used in the manufacture of medical balloons, such as those disclosed in the present application. The balloon may then be molded using commonly known extrusion and blow molding methods, such as those described in the foregoing paragraphs.

In a typical process, a parison comprising graphene is extruded and placed within a hollow mold, which is shaped to correspond to the inflated configuration of the balloon. The parison and/or mold is then heated and pressure is applied to the inner lumen of the parison to stretch and radially expand at least a mid-section of the parison until the tube conforms to the shape of the mold. After the balloon is molded, it may be cooled and the shaped balloon can then be removed from the mold.

The molded balloon generally includes an inflatable portion with a larger outer diameter and a neck portion with a smaller diameter. The balloon may also have one neck portion at the proximal end of the balloon and another neck portion at the distal end of the balloon. As understood by those having ordinary skill in the art, the inflatable portion is adapted to inflate and deflate in response to an inflation medium that is fed to the interior region of the balloon, for example, when the balloon is mounted on a catheter.

The inflatable portion may be cylindrical as shown or may have another shape suitable for particular medical procedures. The neck portion may be adapted to attach the balloon to a catheter using any conventional techniques, such as by inserting the catheter through an inner lumen of a neck region of the balloon.

In some embodiments, there may be an initial stretching step carried out with respect to a portion of the parison before conducting the blow molding step. The initial stretching process may be achieved by heating one end of the parison, such as the proximal end, without heating the mid-section of the parison. The heated end of the parison may be axially stretched without causing the mid-section to be stretched. The opposite end (distal end) of the parison may optionally be heated and stretched in a similar manner. The initial stretching step may be helpful to define the region of the balloon that will form the expanded balloon after blow molding. One or both of the ends of the parison may also be axially stretched during radial expansion of the mid-section of the parison. Alternatively, one or both of the ends of the parison may be held in place during radial expansion of the mid-section of the parison.

With respect to attachment of the balloon to a catheter, any of the presently disclosed medical balloons comprising at least one polymer may be heat bonded, for example, to a catheter after molding. With respect to a balloon wall made solely from graphene or consisting essentially of graphene, the balloon may be secured to the catheter using an adhesive or a thin heat shrink tube.

The presence of graphene in a medical balloon wall will improve the strength and burst pressure of the balloon. The balloon comprising, consisting essentially of, or consisting of graphene will be much stronger than a balloon not comprising graphene in terms of tensile strength, stiffness, and puncture resistance. Such a balloon will also exhibit decreased shrinkage during storage and lower compliance.

In some embodiments, the balloon comprising, consisting essentially of, or consisting of graphene may achieve a high rated burst pressure (RBP). The RBP is the statistically-determined maximum pressure to which a balloon may be inflated without rupturing. Normally, there is 95% confidence that 99.9% of balloons will not burst at or below the RBP upon single inflation. The presently disclosed medical balloon may achieve a RBP of at least about 5 bar, at least about 10 bar, at least about 20 bar, at least about 25 bar, or at least about 30 bar, depending on the number of graphene sheets/layers present.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a device" is intended to include "at least one device" or "one or more devices."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. An inflatable medical balloon comprising:
a balloon wall defining a balloon interior portion and a balloon exterior portion, wherein the balloon wall comprises an inner layer and an outer layer, wherein the outer layer comprises graphene, and wherein the balloon wall excludes a polymer matrix.

2. The inflatable medical balloon of claim 1, wherein the inner layer comprises a member selected from the group consisting of silicone, polyethyleneterephthalate, polyvinyl chloride, polypropylene, polyethylene, polyurethane, polyamides, polyester, latex, natural rubber, synthetic rubber, polyether block amides, and any mixture thereof.

3. The inflatable medical balloon of claim 1, wherein the graphene is selected from the group consisting of pure graphene, modified graphene, and any combination thereof.

4. The inflatable medical balloon of claim 1, wherein a thickness of the balloon wall is from about 50 nm to about 40 µm.

5. A balloon catheter comprising:
a shaft having a proximal portion extending to a distal portion and a lumen formed therethrough; and
the inflatable medical balloon of claim 1 mounted at the distal portion of the shaft, the balloon interior portion being in fluid communication with the lumen of the shaft.

6. The balloon catheter of claim 5, wherein the inflatable balloon is mounted at the distal portion of the shaft using heat bonding, an adhesive, or a heat shrink tube.

7. An inflatable medical balloon comprising:
a balloon wall defining a balloon interior portion and a balloon exterior portion, wherein the balloon wall consists essentially of graphene; wherein the graphene is selected from the group consisting of pure graphene, modified graphene, and any combination thereof.

8. The inflatable medical balloon of claim 7, wherein the balloon wall consists of graphene.

9. The inflatable medical balloon of claim 7, wherein the balloon wall comprises a number of layers, at least one of the number of layers consisting essentially of graphene.

10. The inflatable medical balloon of claim 9, wherein at least one layer consists of graphene.

11. The inflatable medical balloon of claim 7, wherein a thickness of the balloon wall is from about 50 nm to about 1,000 nm.

12. A balloon catheter comprising:
a shaft having a proximal portion extending to a distal portion and a lumen formed therethrough; and
the inflatable medical balloon of claim 7 mounted at the distal portion of the shaft, the balloon interior portion being in fluid communication with the lumen of the shaft.

13. The balloon catheter of claim 12, wherein the inflatable balloon is mounted at the distal portion of the shaft using heat bonding, an adhesive, or a heat shrink tube.

14. An inflatable medical balloon comprising:
a balloon wall defining a balloon interior portion and a balloon exterior portion, wherein the balloon wall comprises an inner layer and an outer layer, wherein the inner layer comprises graphene, and wherein the balloon wall excludes a polymer matrix.

15. The inflatable medical balloon of claim 14, wherein the outer layer comprises a member selected from the group consisting of silicone, polyethyleneterephthalate, polyvinyl chloride, polypropylene, polyethylene, polyurethane, polyamides, polyester, latex, natural rubber, synthetic rubber, polyether block amides, and any mixture thereof.

16. The inflatable medical balloon of claim 14, wherein the outer layer comprises graphene, further wherein the graphene is selected from the group consisting of pure graphene, modified graphene, and any combination thereof.

17. The inflatable medical balloon of claim 14, wherein a thickness of the balloon wall is from about 50 nm to about 1,000 nm.

18. A balloon catheter comprising:
a shaft having a proximal portion extending to a distal portion and a lumen formed therethrough; and
the inflatable medical balloon of claim 14 mounted at the distal portion of the shaft, the balloon interior portion being in fluid communication with the lumen of the shaft.

* * * * *